(12) United States Patent
Anderson et al.

(10) Patent No.: US 10,575,853 B2
(45) Date of Patent: Mar. 3, 2020

(54) EMBOLIC COIL DELIVERY AND RETRIEVAL

(71) Applicant: Boston Scientific Scimed, Inc., Maple Grove, MN (US)

(72) Inventors: James M. Anderson, Corcoran, MN (US); Derek C. Sutermeister, Ham Lake, MN (US); David Raab, Minneapolis, MN (US); Cass Alexander Hanson, St. Paul, MN (US); Timothy A. Ostroot, Cokato, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 565 days.

(21) Appl. No.: 15/004,055

(22) Filed: Jan. 22, 2016

(65) Prior Publication Data

US 2016/0213379 A1    Jul. 28, 2016

Related U.S. Application Data

(60) Provisional application No. 62/106,350, filed on Jan. 22, 2015.

(51) Int. Cl.
*A61B 17/12* (2006.01)

(52) U.S. Cl.
CPC .... *A61B 17/12113* (2013.01); *A61B 17/1214* (2013.01); *A61B 2017/12054* (2013.01)

(58) Field of Classification Search
CPC .. A61F 2/90; A61F 2/844; A61F 2/966; A61F 2002/823; A61B 17/121113; A61B 17/1215; A61B 17/1214; A61B 17/12109; A61B 17/12113
See application file for complete search history.

(56) References Cited

U.S. PATENT DOCUMENTS

| 5,217,484 | A  | * | 6/1993  | Marks      | A61B 17/12022 128/899 |
| 5,609,608 | A  | * | 3/1997  | Benett     | A61B 17/29 606/205 |
| 2003/0004525 | A1 | * | 1/2003  | Cheng      | A61B 17/12022 606/151 |
| 2004/0034363 | A1 | * | 2/2004  | Wilson     | A61B 17/12022 606/108 |
| 2007/0239192 | A1 | * | 10/2007 | Litzenberg | A61B 17/12022 606/191 |

* cited by examiner

*Primary Examiner* — Tuan V Nguyen

(57) ABSTRACT

The present invention provides systems and methods for accurately delivering embolic coils within a body lumen of a patient, as well as recapturing deployed embolic coils for removal or repositioning. In various embodiments, an embolic coil delivery system may include an elongate sheath with a lumen extending therethrough. An elongate shaft may be slidably disposed within the sheath. The shaft may comprise a split-distal end that defines an aperture. The split-distal end may be moveable between a contracted configuration and an expanded configuration. An embolic coil may include a proximal ball-tip that may be reversibly disposed within the aperture of the split-distal end.

20 Claims, 3 Drawing Sheets

EMBOLIC COIL DELIVERY AND RETRIEVAL

CROSS-REFERENCE TO RELATED APPLICATIONS

Figure 1A:
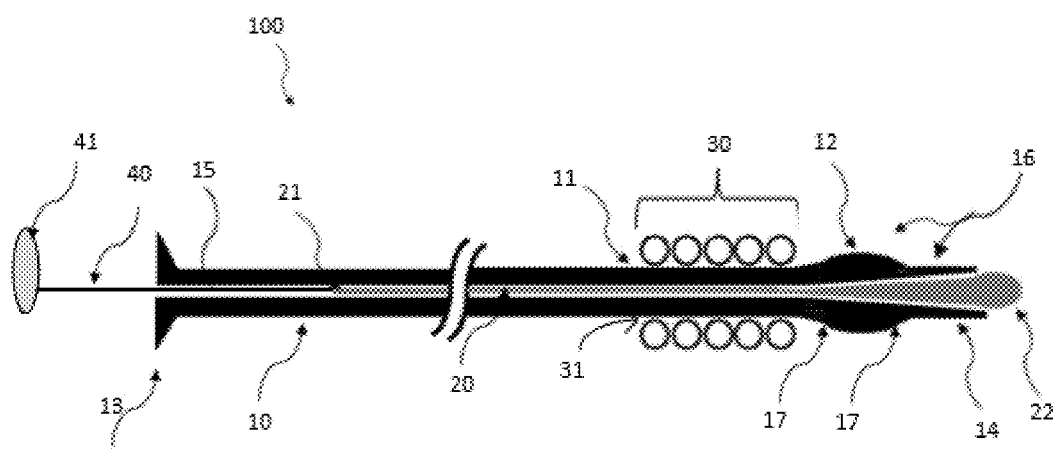

This application claims the benefit of priority under 35 U.S.C. § 119 to U.S. Provisional Patent Application No. 62/106,350 by Anderson, et al. filed Jan. 22, 2015. The entirety of the foregoing application is herein incorporated by reference for all purposes.

FIELD OF THE INVENTION

The present invention relates to the field of medical devices and medical procedures. More particularly, the present invention relates to devices and methods for delivering embolic coils within a body lumen of a patient and recapturing embolic coils post-delivery for removal or relocation.

BACKGROUND

Various medical conditions require partial or complete occlusion of blood vessels or vascular malformations. Embolic coils have proven popular for such applications owing to their ability to be placed at such sites using a variety of percutaneous delivery techniques.

Accurate delivery of the embolic coil to the appropriate site within a body lumen is critical to proper function and favorable patient prognosis. A variety of negative medical outcomes may result from the incomplete or partial occlusion of a vascular malformation, as well as unintended occlusion of nearby vasculature. While conventional systems allow embolic coils to be delivered to a variety of locations within a patient, it remains possible for embolic coils to be delivered improperly (i.e., to the wrong location) or to migrate from the desired placement site following delivery. Unfortunately, once released from the delivery device, it may be difficult, if not impossible, to recapture the embolic coil such that it can be repositioned within (or removed from) the patient.

Accordingly, there is a need for low profile delivery systems capable of deploying an embolic coil in a safe and accurate manner, and recapturing the embolic coil post-delivery for removal or relocation.

SUMMARY OF THE INVENTION

The present invention, in its various aspects, meets an ongoing need in the field of embolization for safe, secure an accurate delivery of embolic coils within a body lumen of a patient. The present invention provides the ability to recapture, remove and/or relocate embolic coils following their delivery.

In one aspect, the present invention relates to a delivery device that includes an elongate first shaft having an outer surface, an inner surface, a proximal end, a distal end and a lumen extending between the proximal and distal ends. The distal end of the elongate first shaft further includes an expandable portion moveable between a contracted and expanded configuration. An elongate second shaft is slidably disposed within the lumen of the elongate first shaft. The elongate second shaft includes a proximal end and a distal end, with the diameter of the distal end being greater than the diameter of the proximal end. A pushrod may be connected to the distal end of the elongate second shaft. An embolic coil, that includes an inner surface and an outer surface, is reversibly coupled to the distal end of the elongate first shaft. In some cases, the outer surface of the elongate first shaft forms an interference fit with the inner surface of the embolic coil when the expandable portion is in the expanded configuration. The outer surface of the elongate first shaft does not substantially contact the inner surface of the embolic coil when the expandable portion is in the contracted configuration in various embodiments. Alternatively or additionally, the expandable portion of the elongate first shaft is in the expanded configuration when the distal end of the elongate second shaft is disposed within the lumen of the elongate first shaft. The expandable portion of the elongate second shaft may also be in the contracted configuration when the distal end of the elongate second shaft is disposed outside the lumen of the elongate first shaft. The outer surface of the elongate first shaft can include, in some cases, at least one outwardly extending protrusion adjacent to a distal end of the embolic coil, which outwardly extending protrusion optionally retains the embolic coil on the outer surface of the elongate first shaft when in the expanded configuration and/or includes an angled surface that slopes away from the embolic coil. The embolic coil may be a substantially cylindrical coil with an inner diameter and an outer diameter. The elongate first shaft has, in some cases, a first outer diameter when in the expanded configuration and a second outer diameter when in the second configuration. The inner diameter of the embolic coil is, optionally, greater than the second outer diameter of the elongate first shaft. The elongate first shaft can be made from a variety of materials in various embodiments, including, for example, nitinol or a shape memory polymer.

In another aspect, the present invention relates to a method of delivering an embolic coil utilizing a delivery device as described above, including the steps of inserting the delivery device into a micro-catheter, advancing the elongate second shaft in a distal direction relative to the elongate first shaft to release the embolic coil from the outer surface of the elongate first shaft, retracting the elongate first shaft to deploy the embolic coil, and removing the delivery device from the micro-catheter. These steps may be repeated as necessary to deliver multiple embolic coils to a particular location (e.g., within a body lumen of a patient).

In yet another aspect, the present invention relates to a delivery device that includes an elongate sheath with a lumen extending therethrough. An elongate shaft is slidably disposed within the elongate sheath. The elongate shaft includes a split distal end. The split-distal end defines an aperture and is moveable between a contracted configuration and an expanded configuration. An embolic coil that includes a proximal ball-tip is reversibly disposed within the aperture of the split-distal end. The split-distal end preferably forms an interference fit with the outer surface of the distal ball-tip of the embolic coil when in the contracted configuration. The split-distal end, when in the expanded configuration, may define an aperture larger than the proximal ball-tip of the embolic coil. The split-distal end, in various embodiments, is in the contracted configuration when the elongate shaft is disposed within the sheath and/or in the expanded configuration when the elongate shaft is disposed outside of the sheath. The split-distal end can in some cases include a ridge (i.e., retaining ridge) configured to engage the distal ball-tip of the embolic coil when in the contracted configuration.

In still another aspect, the present invention relates to a method of delivering an embolic coil into a delivery device as described above, which including the steps of loading an embolic coil into the split-distal end of the delivery device such that the ridge (i.e., retaining ridge) engages the ball-tip proximal to a first winding of the embolic coil, inserting the delivery device into a micro-catheter, advancing the delivery device through the distal tip of the micro-catheter such that the split-distal end of the delivery device moves into an expanded configuration to deploy the embolic coil, and removing the delivery device from the micro-catheter. These steps may be repeated as necessary to deliver multiple embolic coils to a particular location (e.g., within a body lumen of a patient). The embolic coil may be delivered into a vascular malformation such as an aneurysm, and the method optionally includes a step of verifying the positioning of the coil within the patient.

And in another aspect, the present invention relates to a method of recapturing an embolic coil, including the steps of inserting the delivery device described above into a micro-catheter, advancing the micro-catheter (containing the delivery device) adjacent to a deployed embolic coil, advancing the delivery device through the distal tip of the micro-catheter such that the split-distal end of the delivery device transforms into an expanded configuration, and advancing the micro-catheter to the distal tip of the delivery device such that the split-distal end moves in a closed configuration to capture the proximal ball-tip of the embolic coil. The method also includes one or more of removing the recaptured coil and the delivery system from the vasculature of the patient, repositioning the recaptured coil within the vasculature of the patient and/or deploying the repositioned coil within the vasculature of the patient.

DRAWINGS

Non-limiting embodiments of the present invention will be described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

Figure 1B:
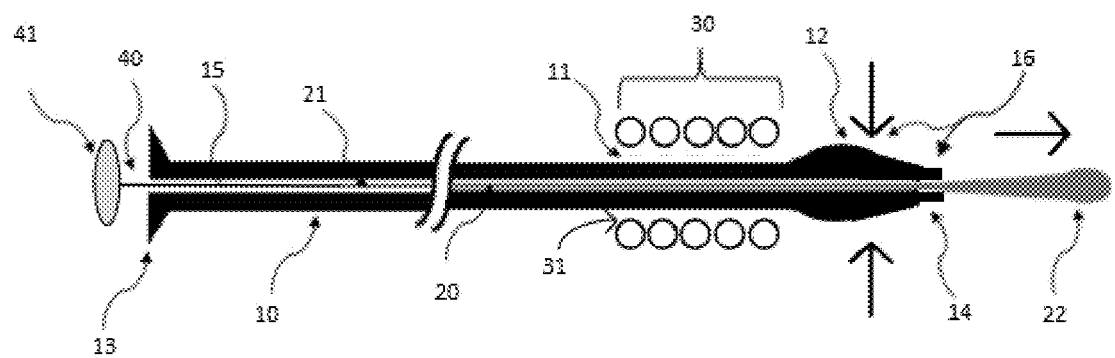
Figure 1C:
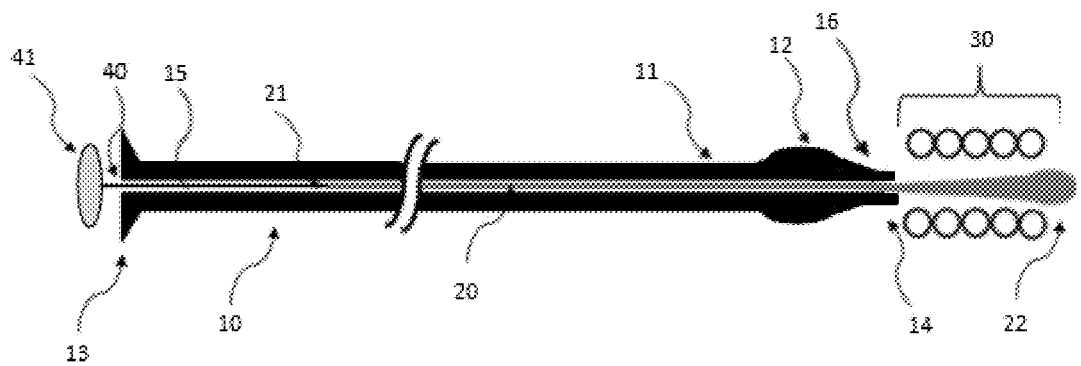

FIGS. 1A-C depict an embolic coil delivery and retrieval system, in accordance with one embodiment of the present invention. When in the expanded configuration, the delivery device exerts outward pressure against the inner surface of an embolic coil reversibly coupled to outer surface of the delivery device (1A). This outward pressure is relieved as the delivery device transitions to a contracted configuration, thereby releasing the embolic coil from the device (1B) for delivery into a lumen of a patient (1C).

Figure 2A:
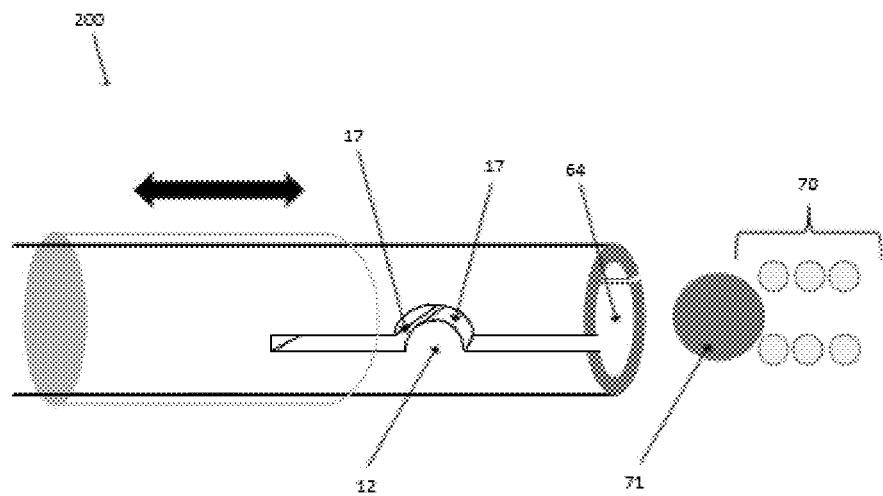
Figure 2B:
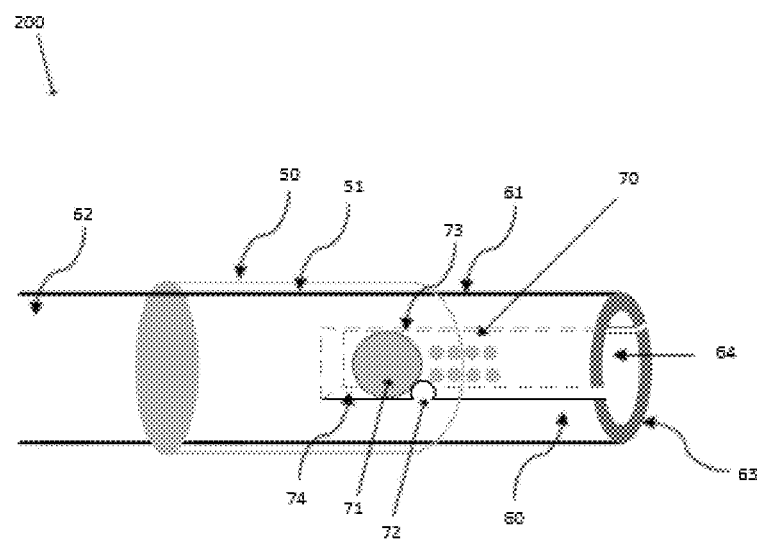

FIGS. 2A-B depict an embolic coil delivery and retrieval system, in accordance with another embodiment of the present invention. The delivery device is depicted in a contracted configuration, with an embolic coil released from (2A) or retained within (2B) the aperture of the split-distal end.

Figure 3A:
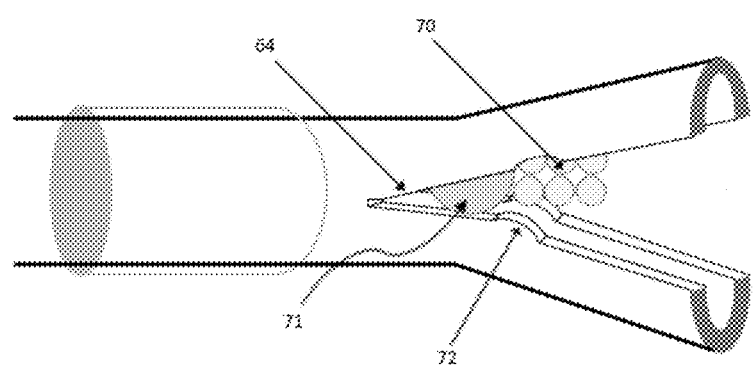
Figure 3B:
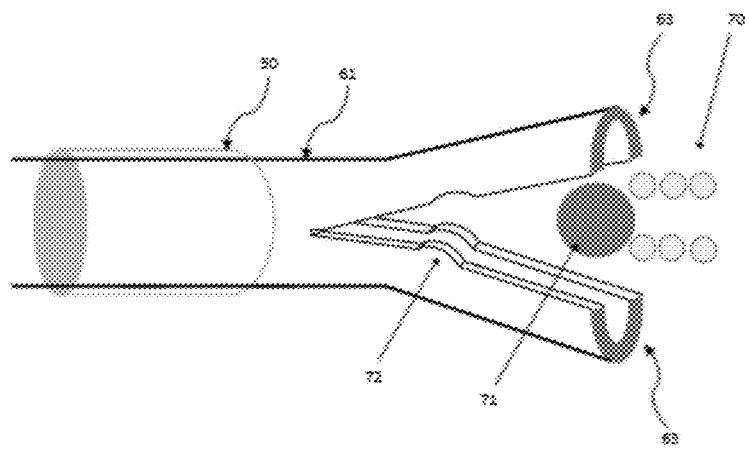

FIGS. 3A-B depict an embolic coil delivery and retrieval system, in accordance with yet another embodiment of the present invention. The delivery device is depicted in an expanded configuration, with the embolic coil retained within (3A) or being released from (3B) the aperture of the split-distal end.

DETAILED DESCRIPTION OF THE PREFERRED EMBODIMENTS

Before the present invention is described in further detail, it is to be understood that the invention is not limited to the particular embodiments described herein, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the invention belongs. Finally, although embodiments of the present invention are described with specific reference to embolic coils, it should be appreciated that the scope of the invention may be applicable to a number of implantable devices requiring delivery to specific location(s) within a patient.

The present invention is generally directed to systems and methods for accurately delivering an embolic coil within a body lumen of a patient; and recapturing embolic coils post-delivery for removal or relocation.

FIGS. 1A-C generally depict a delivery system 100 that includes an inner (second) shaft 20 slidably disposed within the lumen 15 of an outer (first) shaft 10. The distal end 14 of outer shaft 10 includes an expandable portion 16 made from a material that is configured to move between an expanded configuration (FIG. 1A) and a contracted configuration (FIGS. 1B, C). In one embodiment, the expandable portion 16 comprises a shape memory material. At least one, and optionally both, of the inner and outer shafts 10, 20 include a distal ends 12, 22 that taper from a maximal diameter near the distal end to a smaller diameter more proximally. Optionally, the outer shaft 10 is characterized by a wall-thickness that decreases from a maximal value at or near its distal end of the structure to a smaller thickness more proximally.

As illustrated in FIG. 1A, when the distal end of inner shaft 20 is disposed within the outer shaft 10, the larger diameter portion of the tapered region urges the expandable portion 16 into an expanded configuration, thereby forming an interference fit with the inner surface 31 of embolic coil 30 (depicted in a cross-sectional view) disposed on the outer surface 11 of outer shaft 10. The compression force exerted on the inner surface of the embolic coil by the expandable portion is sufficient to retain the embolic coil on the outer surface of the first shaft 10. For example, the embolic coil is retained on the outer surface of first shaft 10 while the delivery system 100 is advanced through the vasculature to a delivery site.

A protrusion 12 on outer surface 11 of outer shaft 10 at a location distal to the embolic coil optionally serves to further secure the embolic coil prior to delivery. Protrusion 12 optionally includes angled surfaces 17 to facilitate smooth delivery of the embolic coil from the delivery device when in the contracted configuration (discussed below), and to ensure that the delivery device advances through the vasculature in a minimally invasive manner.

As illustrated in FIG. 1B, the interaction outlined by FIG. 1A may be reversed by advancing the inner shaft 20 in the distal direction such that the tapered diameter is not disposed within the outer shaft 10, thereby allowing the expandable portion to return to a contracted (i.e., relaxed) configuration (see arrows). Since the inner diameter of the embolic coil is greater than the maximum outer diameter of shaft 10 when in the contracted configuration, the interference fit with the inner surface of the embolic coil is eliminated. As depicted in FIG. 1C, the delivery system may then be retracted proximally such that the embolic coil passes over the distal end 14 of shaft 10 and into an appropriate location within the patient.

In practice, and by way of example, the delivery system with a securely attached embolic coil is advanced through the vasculature of a patient to the site of an aneurysm or vascular malformation. Once positioned at the desired location, a user advances plunger 41 of pushrod 40, attached to the proximal end shaft 20, in the distal direction such that the larger diameter distal portion of shaft 20 slides out of expandable portion 16, thereby allowing the expandable portion to assume the contracted configuration and relieving the compression force exerted against the inner surface of embolic coil 30. Upon verifying that the embolic coil is properly positioned (e.g., by using MRI, X-ray, sonograms etc.) the delivery system (still in the contracted configuration) is retracted through the inner diameter of the embolic coil 30.

In one embodiment, the present invention relates to a method of delivering an embolic coil, including the steps of inserting the delivery system into a micro-catheter, advancing the elongate second shaft 20 in a distal direction 22 relative to the elongate first shaft 10 to release the embolic coil 30 from the outer surface 11 of the elongate first shaft 10, retracting the elongate first shaft 10 to deploy the embolic coil 11, and removing the delivery device from the micro-catheter. These steps may be repeated as necessary to deliver multiple embolic coils to a particular location (e.g., within a body lumen of a patient).

In the event that the recently delivered embolic coil is determined to be improperly positioned, the expandable portion 16 (in the contracted configuration) is advanced distally through the inner diameter of the embolic coil 30 until the entire embolic coil is located proximal to protrusion 12. The user then retracts pushrod 40 proximally such that the larger diameter portion of shaft 20 slides into expandable portion 16, thereby urging expandable portion 16 into the expanded configuration and re-establishing the interference fit against the inner surface of the embolic coil. Once the embolic coil is substantially secured, the delivery device may then be repositioned within the patient and the embolic coil re-delivered to at the proper location using the steps outlined above.

Alternatively, the embolic coil may be repositioned by advancing the expandable portion through less than the full inner diameter of the embolic coil (i.e., through a portion of the inner diameter of the embolic coil). The user then retracts pushrod 40 proximally such that the larger diameter portion of shaft 20 slides into expandable portion 16 with sufficient force to urge protrusion 12 against the inner surface of the embolic coil. Adjusting the proximal pressure exerted on the pushrod allows the user to control/adjust the compression force against exerted against the inner surface of the embolic coil. Once the re-secured embolic coil is successfully repositioned, the user again advances the pushrod in the distal direction until the expandable portion assumes the contracted configuration, at which point the delivery system may be withdrawn from the embolic coil and removed from the patient.

The ability of the expandable portion 16 to exert a retentive force at various locations along the inner surface of the embolic coil represents a significant advantage over other delivery systems because it permits discrete portions along the full length of the embolic coil to be repositioned. For example, if an embolic coil is otherwise properly positioned with an aneurysm, except for a trailing portion that improperly extends outside the aneurysm space, the delivery system may be re-inserted into the portion of the embolic coil that requires repositioning. Similarly, the delivery system may be used to deploy the embolic coil in a stepwise fashion rather than all at once. For example, a portion of the embolic coil may be advanced over the distal end of the expandable portion, at which point the expandable portion is urged into the expanded configuration. The released portion of the embolic coil can then be positioned within an aneurysm. Once the first portion of the embolic coil is successfully delivered, the process can be repeated to release and position another section of the embolic coil. In this manner, the user is able to position (i.e., pack) the embolic coil into the aneurysm in a customized fashion rather than a single releasing event.

It should be emphasized that the above-described embodiments are in no way limited to recently deployed embolic coils, but are also applicable for previously deployed (i.e., months, days or years earlier) embolic coils that require repositioning, removal and/or replacement. For example, the delivery system may be introduced into the vasculature of a patient in the contracted configuration but without an embolic coil disposed on the outer surface. The delivery system is advanced to a site at which an embolic coil was previously delivered and the embolic coil recaptured as described above, and repositioned, removed and/or replaced as necessary.

FIGS. 2A-B and 3A-B illustrate an alternative embodiment of a system for delivering and retrieving an embolic coil. This embodiment is similar to the embodiment depicted in FIG. 1A-C, with the general exception that the embolic device is retained within an aperture of the delivery device by an inward compression force.

FIGS. 2A-B generally depict a delivery system 200 that includes a shaft 60 slidably disposed within a sheath 50 which slidably encloses at least a portion of the length of the shaft 60, as well as an embolic coil 70 that includes proximal ball-tip 71. Shaft 60 includes a proximal end 62 and a split-distal end 63 that defines an aperture 64. The split-distal end 63 is configured to move between an expanded configuration and a contracted configuration. Optionally, the distal end 63 is made from a shape memory material.

As illustrated in FIG. 2A, sheath 50 (e.g., microcatheter) is slidable along the outer surface 61 of shaft 60 in both the proximal and distal directions (see arrow). As sheath 50 advances in the distal direction over at least a portion of aperture 64, the split-distal end 63 is urged into a contracted configuration. As best shown in FIG. 2B, when an embolic coil 70 is disposed within the aperture 64, the inner surfaces (i.e., top 73 and bottom 74 surfaces) of the split-distal end compress against at least a portion of the exterior (i.e., outer) surface of ball-tip 71 to form an interference fit that retains the embolic coil within the delivery device. At least one of the inner surfaces of the split-distal end optionally includes an inwardly extending protrusion 72 (i.e., ridge) positioned to engage the ball-tip 71 proximal to a first winding of the embolic coil to further secure the embolic coil during delivery. As best illustrated by FIG. 2A, protrusion 72 includes a substantially smooth surface 17 to facilitate the release of ball-tip 71 from the delivery device when in the expanded configuration (discussed below).

As illustrated in FIG. 3A, retracting the sheath in the proximal direction, such that it is no longer disposed over the aperture 64, allows the split-distal end to splay outwards and assume the expanded (i.e., relaxed) configuration. With the inward compression force against the exterior surface of the ball-tip relieved (FIG. 3A), the embolic coil releases from the aperture of the split-distal end 63 (FIG. 3B). Once the embolic coil is free of the delivery system, sheath 50 is advanced distally to return the split-distal end to the contracted configuration.

In practice, and by way of example, a delivery system 200 with an embolic coil secured within aperture 64 is advanced through the vasculature of a patient to the site of an aneurysm or vascular malformation. Once positioned at the desired location, a user retracts sheath 50 such that the split-distal end is free to assume the expanded configuration and release the embolic coil. Upon verifying that the embolic coil is properly positioned (e.g., by using MRI, X-ray, sonograms etc.) the user advances the sheath distally such that the split-distal end is returned to the contracted configuration for removal from the patient.

In the event that the delivered embolic coil is determined to be improperly positioned, the delivery system is advanced to within a close proximity of the proximal ball-tip of the embolic coil. The split-distal end is then urged into the expanded configuration by advancing sheath 50 in the proximal direction, as described above. The delivery system is then advanced forward such that the embolic coil is positioned within the aperture of the split-distal end. Once the proximal ball-tip is positioned proximal to protrusion 72, or fully within the aperture 64 if the protrusion is not present, the sheath 50 is again advanced in the distal direction such that the split-distal end is urged into the contracted configuration to re-engage the embolic coil within the aperture. The delivery device may then be repositioned within the patient and the embolic coil re-delivered to the proper location as indicated above.

In one embodiment, the present invention relates to a method of delivering an embolic coil, including the steps of loading an embolic coil 70 into the split-distal end 63 of the delivery device such that the ridge 72 (i.e., retaining ridge) engages the ball-tip 71 proximal to a first winding of the embolic coil 70, inserting the delivery system into a micro-catheter (i.e., sheath 50), advancing the delivery device through the distal tip of the micro-catheter such that the split-distal end 63 of the delivery device moves into an expanded configuration to deploy the embolic coil 70, and removing the delivery device from the micro-catheter. These steps may be repeated as necessary to deliver multiple embolic coils to a particular location (e.g., within a body lumen of a patient).

In another aspect, the present invention relates to a method of recapturing an embolic coil, including the steps of inserting the delivery system into a micro-catheter (i.e., sheath 50), advancing the micro-catheter (containing the delivery device) adjacent to a deployed embolic coil 70, advancing the delivery device through the distal tip of the micro-catheter such that the split-distal end 63 of the delivery device moves into an expanded configuration, and advancing the micro-catheter to the distal tip of the delivery device such that the split-distal end 63 moves in a closed configuration to capture the proximal ball-tip 71 of the embolic coil 70.

It should be emphasized that the above-described embodiments are applicable to previously deployed embolic coils that require repositioning, removal and/or replacement. For example, the delivery system may be introduced into the vasculature of a patient in the contracted configuration but without an embolic coil retained within the aperture of the split-distal end. The delivery system is advanced to a site at which an embolic coil was previously delivered and the embolic coil recaptured as described above and repositioned or removed as necessary.

In one aspect, the expandable portion 16 and/or split-distal end 63 may comprise polymeric and/or metallic materials such as nitinol that exhibit shape memory or superelastic characteristics, or both. As used herein, "nitinol" refers to a class of nickel-titanium alloys recognized for their shape memory and pseudoelastic properties. As a shape memory material, nitinol is able to undergo a reversible thermoelastic transformation between certain metallurgical phases. Similarly, as used herein, "shape memory polymer" refers to a polymeric material that can be activated by the impartation of energy to transition from a first shape to a second shape. In some embodiments, the energy for activation is thermal energy, whereby the polymer has a first shape at a first temperature, and can be activated to assume a different, second shape upon heating to a second temperature. In certain embodiments, the material can further assume a third shape upon heating to a third temperature higher than the second temperature. The polymeric material can be natural, synthetic, or a mixture of natural and synthetic materials. In some embodiments, the polymeric material includes a natural polymer, e.g., zein, casein, gelatin, gluten, serum albumin, collagen, polysaccharides, polyhyaluronic acid, poly(3-hydroxyalkanoates), alginate, dextran, cellulose, collagen or mixtures of these polymers. In some embodiments, the polymeric material includes a synthetic polymer, e.g., chemical derivatives of collagen, chemical derivatives of cellulose, polyphosphazenes, poly (vinyl alcohols), polyamides, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyesters, degradable polymers, polyester amides, polyanhydrides, polycarbonates, polyorthoesters, polylactides, polyglycolides, polysiloxanes, polyurethanes, cellulose derivatives or mixtures of these polymers. In some embodiments, polymeric material includes mixtures of natural and synthetic polymers. In some embodiments, the polymeric material is cross-linked.

The polymer can be, for example, selected from polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and blends thereof.

The shape memory polymer structures described herein can be formed by a variety of techniques. For example, the SMP structures can be formed by extrusion, co-extrusion, molding, e.g., injection molding, co-molding, compression molding, and/or casting. Apertures can be formed by laser ablation or by forming the apertures in the wall of the structure as the structure is molded. Where the structures are to be an integral part of a delivery system or other device, the device can be formed by any of the above methods, or alternatively can be formed by attaching a shape memory polymer to a portion of the device, e.g., by adhesive or welding, such as butt welding.

As indicated throughout the present application, proper positioning of the embolic coil within the patient requires the ability to monitor (i.e., visualize) the location of the delivery device and attached embolic coil. In one aspect, the delivery systems described herein may comprise a radiopaque material, either distributed throughout the entire delivery system or at discrete locations. By way of non-limiting example, a radiopaque material may be included at the distal end 14 of shaft 10 (FIGS. 1A-C), and/or the distal end 63 of shaft 60 (FIG. 2B). Alternatively, or additionally, a radiopaque material may be included in shafts 10 and 60 at locations immediately proximal and immediately distal to the retained coil 30 (FIGS. 1A-B) and/or the retained coil 70

(FIG. 2B), respectively. Various radiopaque materials and their salts and derivatives may be used including, without limitation, bismuth, barium and its salts such as barium sulfate, tantalum, tungsten, gold, platinum and titanium. Additional useful radiopaque materials may be found in U.S. Pat. No. 6,626,936, which is herein incorporated in its entirety by reference. Metallic complexes useful as radiopaque materials are also contemplated. The stent may be selectively made radiopaque at desired areas along the wire or made be fully radiopaque, depending on the desired end-product and application.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An embolic coil delivery system, comprising:
   an elongate sheath with a lumen extending therethrough,
   an elongate shaft slidably disposed within the sheath, the shaft comprising a split-distal end that defines an aperture, the split-distal end having a protrusion on a first thickness of a wall of the elongate shaft and a cavity on a second thickness of a wall of the elongate shaft configured to at least partially receive the protrusion, wherein the split-distal end is moveable between a contracted configuration and an expanded configuration;
   an embolic coil including a proximal ball-tip having a circumference, the embolic coil reversibly disposed within the aperture of the split-distal end;
   wherein the split-distal end contacts a majority of the circumference of the proximal ball-tip in the contracted configuration; and
   wherein the expanded configuration of the split-distal end is a relaxed configuration.

2. The delivery system of claim 1, wherein split-distal end forms an interference fit with an outer surface of the proximal ball-tip of the embolic coil when in the contracted configuration.

3. The delivery system of claim 1, wherein the split-distal end, when in the expanded configuration, defines an aperture larger than the proximal ball-tip of the embolic coil.

4. The delivery system of claim 1, wherein the split-distal end is in the contracted configuration when the elongate shaft is disposed within the sheath.

5. The delivery system of claim 1, wherein the split-distal end is in the expanded configuration when the elongate shaft is disposed outside of the sheath.

6. The delivery system of claim 1, wherein the protrusion is configured to engage the proximal ball-tip of the embolic coil when the split-distal end is in the contracted configuration.

7. A method of delivering an embolic coil, the method utilizing a delivery system, comprising an elongate sheath with a lumen extending therethrough, an elongate shaft slidably disposed within the sheath, the shaft in turn comprising a split-distal end that defines an aperture, the split-distal end having a protrusion on a first thickness of a wall of the elongate shaft and a cavity on a second thickness of a wall of the elongate shaft configured to at least partially receive the protrusion, and wherein the split-distal end is moveable between a contracted configuration and an expanded configuration, the method comprising:
   loading an embolic coil comprising a proximal ball-tip having a circumference into the split-distal end of the elongate shaft proximal to the protrusion such that the split-distal end contacts a majority of the circumference of the proximal ball-tip in the contracted configuration;
   inserting the elongate shaft into the elongate sheath such that the elongate shaft moves to the contracted configuration to form an interference fit with the proximal ball-tip;
   positioning the delivery system within a vasculature of a patient;
   retracting the elongate sheath proximally such that the split-distal end of the elongate shaft moves into the expanded configuration to deploy the embolic coil; and advancing the elongate sheath distally such that the split-distal end of the elongate shaft transforms into the contracted configuration.

8. The method of claim 7, further comprising removing the delivery system from the vasculature of the patient.

9. The method of claim 7, wherein the embolic coil is deployed into a vascular malformation.

10. The method of claim 9, wherein the vascular malformation is an aneurysm.

11. The method of claim 9, further comprising verifying that the embolic coil is properly positioned within the vascular malformation.

12. The method of claim 9, wherein multiple embolic coils are deployed into the vascular malformation.

13. The method of claim 7, wherein the protrusion is configured to engage the proximal ball-tip proximal to a first winding of the embolic coil when the elongate shaft is in the contracted configuration.

14. A method of recapturing an embolic coil, the method utilizing a retrieval system, comprising an elongate sheath with a lumen extending therethrough, an elongate shaft slidably disposed within the sheath, the shaft in turn comprising a split-distal end that defines an aperture, the split-distal end having a protrusion on a first thickness of a wall of the elongate shaft and a cavity on a second thickness of a wall of the elongate shaft configured to at least partially receive the protrusion, and wherein the split-distal end is moveable between a contracted configuration and an expanded configuration, the method comprising:

inserting the elongate shaft into the elongate sheath such that the split-distal end of the elongate shaft moves to the contracted configuration;

positioning the retrieval system adjacent to an embolic coil having a proximal ball-tip with a circumference within a vasculature of a patient;

retracting the elongate sheath proximally such that the split-distal end of the elongate shaft moves into the expanded configuration;

advancing the retrieval system such that at least a portion of the embolic coil is disposed within the aperture of the split-distal end; and advancing the elongate sheath distally such that the split distal-end of the elongate shaft transforms into the contracted configuration with the split-distal end contacting a majority of the circumference of the proximal ball-tip proximal to the protrusion in the contracted configuration to recapture the embolic coil.

15. The method of claim 14, further comprising removing the retrieval system and recaptured embolic coil from the vasculature of the patient.

16. The method of claim 14, further comprising repositioning the recaptured embolic coil within the vasculature of the patient.

17. The method of claim 16, further comprising deploying the repositioned embolic coil within the vasculature of the patient.

18. The method of claim 17, further comprising verifying that the deployed embolic coil is properly repositioned within the vasculature of the patient.

19. The method of claim 14, wherein the split-distal end forms an interference fit with an outer surface of the proximal ball-tip of the embolic coil when in the contracted configuration.

20. The method of claim 14, wherein the protrusion is configured to engage the proximal ball-tip proximal to a first winding of the embolic coil when the elongate shaft is in the contracted configuration.

* * * * *